United States Patent [19]
Flumene et al.

[11] Patent Number: 5,562,634
[45] Date of Patent: Oct. 8, 1996

[54] INTRAVENOUS CATHETER WITH AUTOMATICALLY RETRACTING NEEDLE-GUIDE

[75] Inventors: Antonio G. Flumene; Giuseppe Pilo, both of Sassari; Giorgio Muschio, Martinengo, all of Italy

[73] Assignee: Giuseppe Pilo, Sassari, Italy

[21] Appl. No.: 305,720

[22] Filed: Sep. 14, 1994

[30] Foreign Application Priority Data

Sep. 16, 1993 [IT] Italy .................................. SS93U0002

[51] Int. Cl.$^6$ ............................................ A61M 5/00
[52] U.S. Cl. ........................ 604/171; 604/164; 604/198
[58] Field of Search .................... 604/110, 158, 604/164, 168, 171, 195

[56] References Cited

U.S. PATENT DOCUMENTS

| | | | |
|---|---|---|---|
| 4,747,831 | 5/1988 | Kulli | 604/110 |
| 4,832,696 | 5/1989 | Luther et al. | 604/164 |
| 4,944,728 | 7/1990 | Carrell et al. | 604/168 |
| 5,000,740 | 3/1991 | Ducharme et al. | 604/168 |
| 5,120,310 | 6/1992 | Shaw | 604/110 |
| 5,205,829 | 4/1993 | Lituchy | 604/164 |
| 5,336,198 | 8/1994 | Silver et al. | 604/110 |
| 5,376,075 | 12/1994 | Haughton et al. | 604/171 |

*Primary Examiner*—John D. Yasko
*Assistant Examiner*—Laird J. Knights
*Attorney, Agent, or Firm*—Merchant, Gould, Smith, Edell, Welter & Schmidt, P.A.

[57] ABSTRACT

An intravenous catheter is provided with a cannula and a needle-guide for the cannula. A support carries the needle-guide, and has a first end from which the needle-guide extends. The support is carried in a sheath, having a diameter sufficient to permit sliding of the support and having a length sufficient to accept the full length of the needle-guide. A retractor continuously urges the support to a position in which the needle-guide is withdrawn into the sheath. The sheath has a first end which defines an opening through which the first end of the support extends, and the sheath is capable of reducing the size of the opening upon insertion of the first end of the sheath into the cannula to grip the support, and returns to its original size upon withdrawal of the first end from the cannula to release the support and permit the withdrawal of the needle-guide into the sheath under the action of the retractor. This provides automatic and involuntary withdrawal of the needle-guide into the protective sheath, reducing the chances of injury.

10 Claims, 3 Drawing Sheets

5,562,634

INTRAVENOUS CATHETER WITH AUTOMATICALLY RETRACTING NEEDLE-GUIDE

BACKGROUND OF THE INVENTION

The present invention is directed to improving the safety of intravenous catheters, especially to reduce the risk of accidental injury after insertion of the catheter or in discarding of the used needle-guide of the catheter.

Catheters for intravenous use typically include a needle-guide, i.e. a metal mandril, covered by a flexible plastic cannula. The needle-guide and cannula are inserted into the patient's vein, whereupon the needle-guide is removed to permit connection of the infusion drip apparatus to the cannula.

After the removal from the cannula, the sharp needle-guide remains exposed, thereby creating a risk of accidental injury to the technician or other workers in the area if the needle-guide is mishandled. The danger of transmission of infection to hospital and health service staff in this manner has become quite troublesome in recent years. This has been particularly true in the cases of diseases such as AIDS and Hepatitis B and C, for which the risks have reached distressing levels. While educational programs such as Universal Precautions and the use of rigid containers have been implemented, these have only marginally reduced the problems of accidental injuries.

Other systems for reducing the danger of accidental injury have also been proposed. For example, U.S. Pat. No. 4,832,696 proposes a system in which the needle guide is manually inserted into a protection hood after use. U.S. Pat. No. 4,747,831 suggests a system where the needle-guide can be retracted through a trigger device. Neither system is totally satisfactory, since in each case some voluntary action on the part of the technician is necessary, and therefore the danger from the exposed needle remains in the event the technician fails to undertake the necessary step.

SUMMARY OF THE INVENTION

The object of the present invention is to provide an intravenous catheter in which the needle guide is involuntarily, automatically and almost immediately after use rendered incapable of injuring the health care workers. This object and others are obtained by providing an intravenous catheter which has a protective sheath for the needle-guide. The needle-guide is subjected to a force which always is urging the needle-guide to the retracted position. Prior to use, the needle-guide is held against the retracting force in an exposed position. Removal of the needle-guide from the cannula automatically releases the holding force, whereby the needle-guide is automatically retracted into the protective sheath. The construction of the present catheter is easily accomplished and requires no unusual manufacturing procedures. The catheter can easily be used in accordance with present techniques, and thus requires no special training for use. The present invention is applicable to a wide variety of catheters.

DETAILED DESCRIPTION

Figure 1:
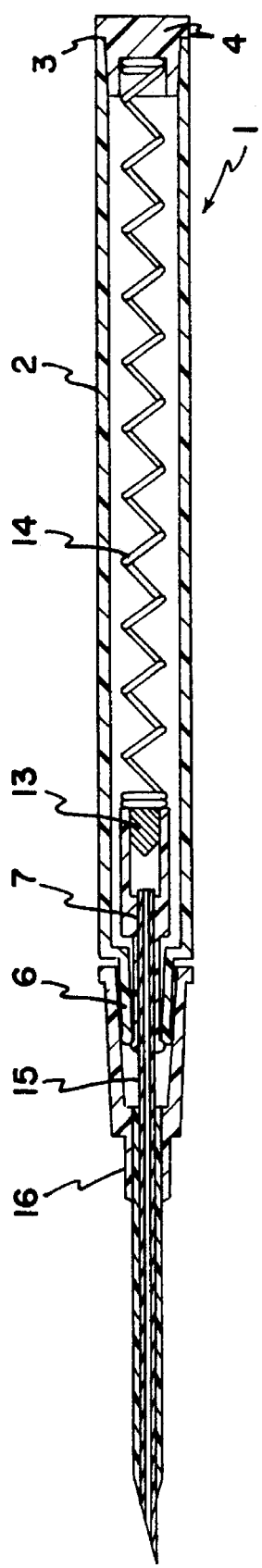
FIG. 1 is a longitudinal sectional view of the intravenous catheter of the present invention prior to use.
Figure 2:
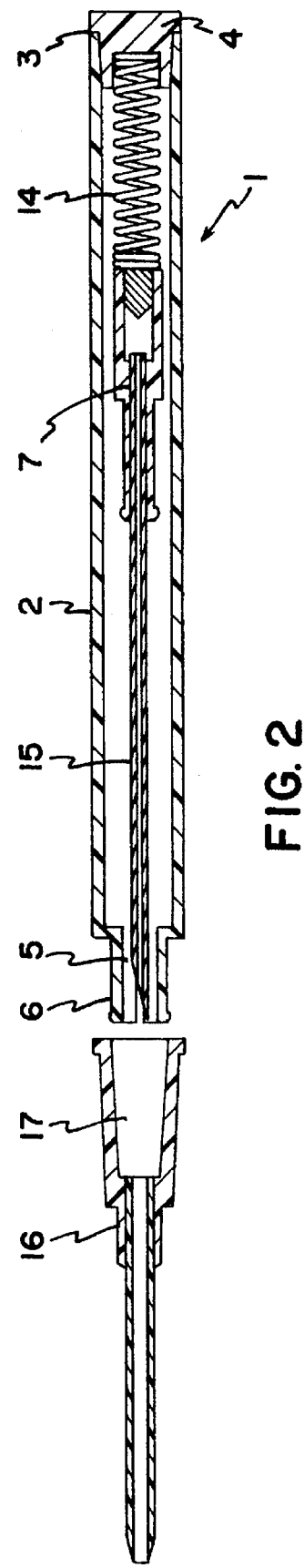
FIG. 2 is a view similar to FIG. 1, taken after the needle-guide has been removed from the cannula.
Figure 3:
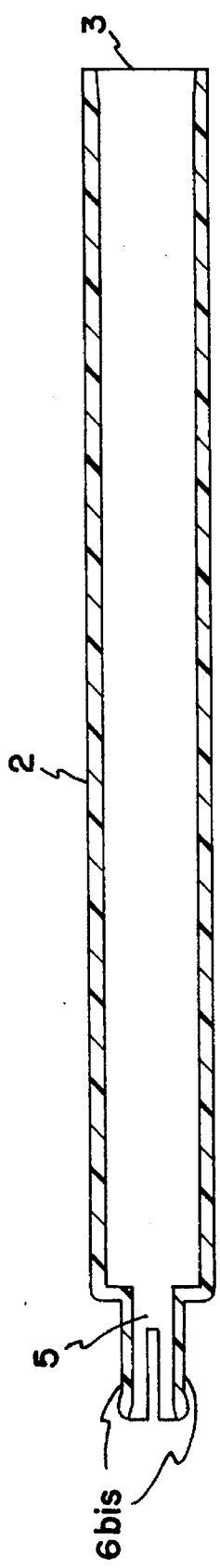
FIG. 3 is an enlarged longitudinal sectional view of the safety sheath used in the present catheter.

Referring to FIGS. 1–3, the catheter of the present invention 1 includes a sheath 2. The sheath 2 is hollow and has an inside diameter sufficiently great to permit the sliding of needle-guide support 7 and retractor 14 inside of the sheath. The sheath 2 has an open end 3, which is closed by stopper 4. As can be seen in the drawings, in the illustrated embodiment, the stopper 4 also serves as the anchor for the retractor 14.

Figure 4:
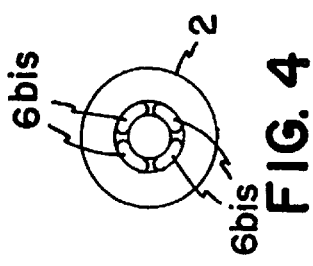
FIG. 4 is an enlarged end view of the safety sheath.

The opposite end of the sheath is provided with a tip 6, which defines an opening 5 having a diameter less than that of the sheath 2, through which the needle-guide 15 and a portion of the needle-guide support 7 extend prior to removal of the needle-guide from the cannula 16. Referring to FIG. 4, it can be seen that the tip is composed of a plurality of independent components 6b is (four in number in the illustrated embodiment). Each of the independent components is separated from the adjacent components by a longitudinally-extending gap. In assembly of the catheter, this permits the components 6b is to be urged toward each other to define an opening 5 of reduced diameter when the tip 6 is inserted into the frusto-conical cavity 17 of catheter cannula 16. However, since the components 6b is are of a resilient construction, the components will return to their original positions when the restraining force is removed. The present invention is suitable for use with any of the cannulae commonly used in this field.

Figure 6:
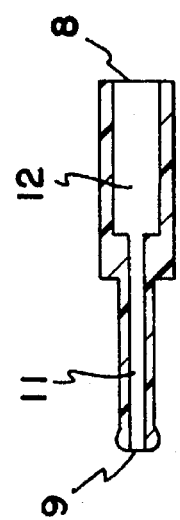
FIG. 6 is an enlarged longitudinal sectional view of the support of FIG. 5.
Figure 5:
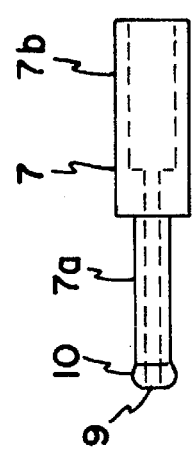
FIG. 5 is a side view of a needle-guide support used in the present catheter.

Needle-guide 15 is carried by support 7. As seen in FIGS. 5 and 6, the support 7 includes two coaxial cylindrical portions 7a and 7b. Portion 7a has a diameter small enough to permit it to pass through the opening 5 in the sheath end and through the tip 6. Portion 7a is provided with a central cavity 11 into which the needle-guide is inserted. The end 9 of the support is provided with a lip 10, which is capable of engaging the tip components 6b is when the needle-guide is in the cannula. See FIG. 7.

Portion 7b has a diameter which is small enough to permit it to move in the sheath 2, but large enough that it does not pass through the opening 5 in the sheath end. Portion 7b is provided with a central cavity 12 which can act as a blood control chamber. The open end 8 of the cavity 12 can be closed with a stopper 13, which is made of a material which can absorb blood, but which permits the passage of air. It is also possible to provide the stopper 13 with a second anchor for the retractor 14.

The retractor 14 may be, for example, a cylindrical spring. Other types of retractors can be used, as long as a continuous withdrawing force is exerted on the support 7. In the case of the illustrated spring, one end is fixed to the support 7, more precisely to the stopper 13 which engages the support in the illustrated embodiment, while the other is fixed to the sheath, more precisely to the stopper 4 which engages the sheath in the illustrated embodiment.

Figure 7:
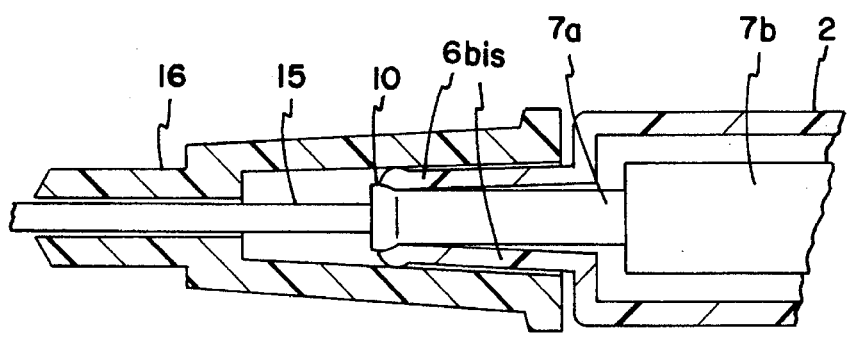
FIGS. 7 and 8 are enlarged longitudinal sectional views of the connection between the safety sheath and the cannula before and after removal of the needle-guide from the cannula.
Figure 8:
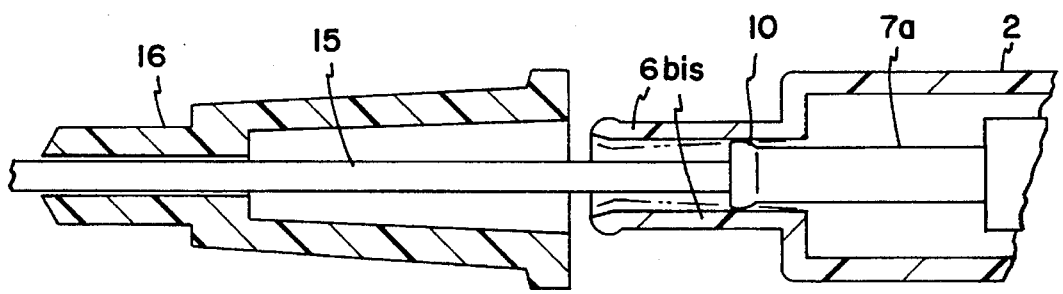

FIG. 7 shows the catheter of the present invention in the assembled condition, with the broken lines illustrating the position of the tip components 6b is prior to assembly. FIG. 8 shows the catheter as the needle-guide is being removed from the cannula, with the broken lines illustrating the position of the tip components 6b is in the assembled position. Referring to FIGS. 7 and 8, when the catheter of the present invention is assembled, the insertion of the tip 6 into the frusto-conical wall of the cavity 17 of the cannula urges the tip components 6b is toward each other. This effectively reduces the size of the opening 5 in the tip and causes the tip 6 to tightly grip the end 9 of the needle-guide support 7. This prevents the retraction of the needle guide by the retractor 14. Thus, the needle-guide is held in the exposed position. This gripping is facilitated by the provision of lip 10 on the end 9. If desired, a removable auxiliary sheath (not shown) can be provided on the needle-guide or cannula to provide protection while the catheter is handled before use.

After the needle-guide and cannula have been inserted in the blood vessel of the patient, the needle-guide is removed by pulling on the sheath 2. As the tip 6 is removed from the frusto-conical cavity 17, the resilient tip components 6b is move outwardly toward their original positions prior to assembly, thereby effectively increasing the size of the opening 5 in the tip. When the components move sufficiently to define a diameter which is greater than that of the lip 10 of the support end 9, the obstacle to the force applied by the retractor 14 is removed. Thus, this movement of the tip components permits the support 7 to be withdrawn under the force exerted by the retractor, thereby quickly and automatically withdrawing needle-guide 15 to the interior of sheath 2, as shown in FIG. 2. The force exerted by the retractor 14 will tend to retain the needle-guide within the sheath 2. The sheath 2, with the needle-guide inside, can then be discarded.

This withdrawing takes place without any voluntary action by the technician. Thus, the present invention provides a disposable product which is simple and effective in use and suited to the needs of the health care industry.

While a detailed description of the invention has been provided above, the present invention is not limited thereto, and modifications will be apparent to those skilled in the art which do not depart from the spirit of the present invention. The invention is defined by the appended claims.

What is claimed is:

1. An intravenous catheter, comprising:

a cannula;

a needle-guide for the cannula;

a support for carrying the needle-guide, having a first end from which the needle-guide extends;

a sheath in which the support is carried, having a diameter sufficient to permit sliding of the support and having a length sufficient to accept the full length of the needle-guide;

a retractor for continuously urging the support to a position in which the needle-guide is withdrawn into the sheath;

said sheath having a first end and a tip at said first end of the sheath which defines an opening, the tip comprising a plurality of resilient tip components, the sheath being capable of reducing the size of the opening upon insertion of the first end of the sheath into the cannula to provide a holding force to prevent withdrawal of the support by the retractor, and being capable of enlarging the opening upon withdrawal of the first end from the cannula to release the holding force and permit the withdrawal of the needle-guide into the sheath under the action of the retractor.

2. The catheter of claim 1, further comprising a lip on the first end of the support which is engaged by the tip to hold the support while the first end of the sheath is inserted in the cannula.

3. The catheter of claim 1, wherein the retractor is a spring.

4. The catheter of claim 1, wherein the support comprises a large diameter portion and a small diameter portion, the small diameter portion comprising said first end of the support and having a diameter smaller than the diameter of the opening, the large diameter portion having a diameter which is smaller than the diameter of the sheath, but larger than the diameter of the opening.

5. The catheter of claim 4, wherein the small diameter portion of the support is provided with a central cavity in which the needle-guide is inserted.

6. The catheter of claim 5, wherein the large diameter portion is provided with a central cavity which is in fluid communication with the cavity of the small diameter portion.

7. The catheter of claim 1, wherein the retractor has a first end which is anchored to the sheath and a second end which is anchored to the support.

8. The catheter of claim 7, wherein the sheath has a second end which is provided with an opening which is closed by a first stopper, the retractor being anchored to said first stopper, the support having an opening which is closed by a second stopper, the retractor being anchored to said second stopper.

9. The catheter of claim 1, wherein the cannula is provided with a frusto-conical cavity in which the first end of the sheath is inserted.

10. The catheter of claim 4, wherein the small diameter portion of the support has an outwardly-tapered end.

\* \* \* \* \*